(12) United States Patent
Martin

(10) Patent No.: US 7,745,210 B2
(45) Date of Patent: Jun. 29, 2010

(54) FLUID FLOW DIVERTER FOR CELL CULTURE VESSEL

(75) Inventor: Gregory Roger Martin, Acton, ME (US)

(73) Assignee: Corning Incorporated, Corning, NY (US)

( * ) Notice: Subject to any disclaimer, the term of this patent is extended or adjusted under 35 U.S.C. 154(b) by 1007 days.

(21) Appl. No.: 11/478,823

(22) Filed: Jun. 30, 2006

(65) Prior Publication Data

US 2008/0003671 A1    Jan. 3, 2008

(51) Int. Cl.
*C12M 1/24* (2006.01)

(52) U.S. Cl. .............. 435/304.1; 435/304.2; 435/304.3; 422/102; 422/910; 422/912; 215/40; 222/572

(58) Field of Classification Search .............. 435/288.1, 435/288.2, 304.1, 304.2, 304.3; 422/102, 422/910, 912; 215/6, 40; 222/572, 573
See application file for complete search history.

(56) References Cited

U.S. PATENT DOCUMENTS

| | | | |
|---|---|---|---|
| 4,225,671 A | 9/1980 | Puchinger et al. .............. 435/71 |
| 4,272,768 A * | 6/1981 | Rookard, Jr. .................... 342/7 |
| 4,296,205 A | 10/1981 | Verma ........................ 435/240 |
| 4,661,455 A | 4/1987 | Hubbard ...................... 435/240 |
| 4,734,373 A | 3/1988 | Bartal ........................ 435/296 |
| 4,748,124 A | 5/1988 | Vogler .................. 435/240.241 |
| 4,770,854 A | 9/1988 | Lyman ........................ 422/102 |
| 4,839,292 A | 6/1989 | Cremonese ................. 435/313 |
| 4,938,196 A | 7/1990 | Hoshi et al. .................. 123/489 |
| 4,945,203 A | 7/1990 | Soodak et al. ......... 219/121.64 |
| 5,026,650 A | 6/1991 | Schwarz et al. ............. 435/286 |
| 5,047,347 A | 9/1991 | Cline ........................ 435/296 |
| 5,079,168 A | 1/1992 | Amiot ........................ 437/284 |
| 5,139,946 A | 8/1992 | Howell et al. ............ 435/240.2 |
| 5,149,649 A | 9/1992 | Miyamori et al. ...... 435/240.242 |
| 5,153,131 A | 10/1992 | Wolf et al. ............. 435/240.24 |
| 5,242,066 A * | 9/1993 | Kelsey ........................ 215/379 |
| 5,310,676 A | 5/1994 | Johansson et al. ........... 435/285 |
| 5,330,908 A | 7/1994 | Spaulding .............. 435/240.24 |
| 5,416,022 A | 5/1995 | Amiot ........................ 435/284 |

(Continued)

FOREIGN PATENT DOCUMENTS

EP    155237 B1    5/1989

(Continued)

OTHER PUBLICATIONS

E. Metzen, M. Wolff, J. Fandrey, and W. Jelkmann, Pericellular PO2 and O2 consumption in monolayer cell cultures, Respiration Physiology 100 (1995) 101-106.

(Continued)

*Primary Examiner*—William H Beisner
(74) *Attorney, Agent, or Firm*—Susan S. Wilks

(57) ABSTRACT

A vessel for culturing of cells is disclosed. The vessel is capable of exhausting substantially all liquid material from the vessel's internal volume through an outlet port. A flange incorporated with the outlet port is utilized as a flow diverter for removing liquid media from internal surfaces of the vessel. The flange also engages the vessel body so that the flow of a liquid medium is directed outward from the internal surfaces of the vessel through the outlet port. The top surface, flange base, and planar surfaces of the flange further assist to redirect surface tension of the fluid toward the port.

15 Claims, 2 Drawing Sheets

U.S. PATENT DOCUMENTS

| | | | | |
|---|---|---|---|---|
| 5,437,998 | A | 8/1995 | Schwarz et al. | 435/286 |
| 5,476,573 | A | 12/1995 | Hirose et al. | 202/197 |
| 5,523,236 | A | 6/1996 | Nuzzo | 435/304.1 |
| 5,527,705 | A | 6/1996 | Mussi et al. | 435/297.1 |
| 5,565,353 | A | 10/1996 | Klebe et al. | 435/240.25 |
| 5,589,112 | A | 12/1996 | Spaulding | 264/413 |
| 5,597,731 | A | 1/1997 | Young et al. | 435/284.1 |
| 5,602,028 | A | 2/1997 | Minchinton | 435/401 |
| 5,627,070 | A | 5/1997 | Gruenberg | 435/786.5 |
| 5,658,797 | A | 8/1997 | Bader | 435/284.1 |
| 5,686,301 | A | 11/1997 | Falkenberg et al. | 435/297.1 |
| 5,686,304 | A | 11/1997 | Codner | 435/325 |
| 5,693,537 | A | 12/1997 | Wilson et al. | 435/401 |
| 5,702,941 | A | 12/1997 | Schwarz | 435/243 |
| 5,714,384 | A | 2/1998 | Wilson et al. | 435/401 |
| 5,763,261 | A | 6/1998 | Gruenberg | 435/286.5 |
| 5,763,275 | A | 6/1998 | Nagels et al. | 435/373 |
| 5,763,279 | A | 6/1998 | Schwarz et al. | 435/383 |
| 5,783,440 | A | 7/1998 | Stevens | 435/304.3 |
| 5,786,215 | A | 7/1998 | Brown et al. | 435/401 |
| 5,801,054 | A | 9/1998 | Kiel | 435/297.5 |
| 5,912,177 | A | 6/1999 | Turner et al. | 435/455 |
| 5,924,583 | A | 7/1999 | Stevens et al. | 215/40 |
| 6,107,085 | A | 8/2000 | Coughlin et al. | 435/299.1 |
| 6,114,165 | A | 9/2000 | Cai et al. | 435/304.3 |
| 6,190,913 | B1 | 2/2001 | Singh | 435/394 |
| 6,297,046 | B1 | 10/2001 | Smith et al. | 435/297.5 |
| 6,323,022 | B1 | 11/2001 | Chang et al. | 435/286.5 |
| 6,410,309 | B1 | 6/2002 | Barbera-Guillem et al. | 435/297.5 |
| 6,450,351 | B1 * | 9/2002 | Thompson | 215/6 |
| 6,455,310 | B1 | 9/2002 | Barbera-Guillem | 435/383 |
| 6,465,243 | B2 | 10/2002 | Okada et al. | 435/301.1 |
| 6,468,792 | B1 | 10/2002 | Bader | 435/325 |
| 6,518,035 | B1 | 2/2003 | Ashby et al. | 435/18 |
| 6,548,263 | B1 | 4/2003 | Kapur et al. | 435/7.2 |
| 6,555,365 | B2 | 4/2003 | Barbera-Guillem et al. | 435/303.1 |
| 6,569,675 | B2 | 5/2003 | Wall et al. | 435/304.2 |
| 6,576,458 | B1 | 6/2003 | Sarem et al. | 435/286.5 |
| 6,588,586 | B2 | 7/2003 | Abasolo et al. | 206/204 |
| 6,593,136 | B1 | 7/2003 | Geiss | 435/325 |
| 6,653,124 | B1 | 11/2003 | Freeman | 435/297.1 |
| 6,673,595 | B2 | 1/2004 | Barbera-Guillem | 435/286.2 |
| 6,759,245 | B1 | 7/2004 | Toner et al. | 435/401 |
| 6,794,184 | B1 | 9/2004 | Mohr et al. | 435/294.1 |
| 6,811,752 | B2 | 11/2004 | Barbera-Guillem | 422/100 |
| 6,818,438 | B2 | 11/2004 | Muser | 435/304.3 |
| 6,821,772 | B2 | 11/2004 | Barbera-Guillem et al. | 435/297.5 |
| 6,841,384 | B2 | 1/2005 | Robbins, Jr. | 435/325 |
| 6,855,542 | B2 | 2/2005 | DiMilla et al. | 435/289.1 |
| 6,908,767 | B2 | 6/2005 | Bader | 435/395 |
| 7,022,518 | B1 | 4/2006 | Feye | 435/297.1 |
| 7,078,228 | B2 | 7/2006 | Lacey et al. | 435/288.1 |
| 7,160,687 | B1 | 1/2007 | Kapur et al. | 435/7.2 |
| 7,192,769 | B2 | 3/2007 | Pykett et al. | 435/373 |
| 7,195,758 | B2 | 3/2007 | Schultze et al. | 424/93.71 |
| 2002/0039785 | A1 | 4/2002 | Schroeder et al. | 435/304.3 |
| 2002/0110905 | A1 | 8/2002 | Barbera-Guillem et al. | 435/294.1 |
| 2003/0008388 | A1 | 1/2003 | Barbera-Guillem et al. | 435/297.5 |
| 2003/0008389 | A1 | 1/2003 | Carll | 435/302.1 |
| 2003/0040104 | A1 | 2/2003 | Barbera-Guillem | 435/286.2 |
| 2003/0143727 | A1 | 7/2003 | Chang | 435/289.1 |
| 2004/0029266 | A1 | 2/2004 | Barbera-Guillem | 435/297.5 |
| 2004/0043481 | A1 | 3/2004 | Wilson | 435/297.1 |
| 2004/0132175 | A1 | 7/2004 | Vetillard et al. | 435/297.1 |
| 2004/0259242 | A1 * | 12/2004 | Malinge et al. | 435/325 |
| 2005/0009179 | A1 | 1/2005 | Gemmiti et al. | 435/420 |
| 2005/0032208 | A1 | 2/2005 | Oh et al. | 435/366 |
| 2005/0077225 | A1 | 4/2005 | Usher et al. | 210/321.6 |
| 2005/0101009 | A1 | 5/2005 | Wilson et al. | 435/295.3 |
| 2005/0106717 | A1 | 5/2005 | Wilson et al. | 435/297.5 |
| 2005/0169962 | A1 | 8/2005 | Bhatia et al. | 424/423 |
| 2005/0260745 | A1 | 11/2005 | Domansky et al. | 435/294.1 |
| 2006/0003436 | A1 | 1/2006 | DiMilla et al. | 435/284.1 |
| 2006/0019361 | A1 | 1/2006 | Ng et al. | 435/177 |
| 2006/0031955 | A1 | 2/2006 | West et al. | 800/24 |
| 2006/0112438 | A1 | 5/2006 | West et al. | 800/17 |
| 2006/0121606 | A1 | 6/2006 | Ito et al. | 435/325 |
| 2006/0136182 | A1 | 6/2006 | Vacanti et al. | 703/11 |
| 2006/0141617 | A1 | 6/2006 | Desai et al. | 435/325 |
| 2006/0252150 | A1 | 11/2006 | Cheng | 435/372 |
| 2007/0026516 | A1 | 2/2007 | Martin et al. | 435/297.5 |
| 2007/0166822 | A1 | 7/2007 | Kenney et al. | 435/325 |

FOREIGN PATENT DOCUMENTS

| | | |
|---|---|---|
| EP | 0 725 134 | 8/1996 |
| EP | 0 890 636 | 10/2001 |
| GB | 1 539 263 | 1/1979 |
| JP | 04237488 A * | 8/1992 |
| WO | WO 90/05179 | 5/1990 |
| WO | WO 91/15570 | 10/1991 |
| WO | WO 00/56870 | 9/2000 |
| WO | WO 00/78932 | 12/2000 |
| WO | WO 01/92462 | 12/2001 |
| WO | WO/02/066595 | 8/2002 |
| WO | WO 03/085080 | 10/2003 |
| WO | WO 2004/106484 | 12/2004 |
| WO | WO 2005/035728 | 4/2005 |

OTHER PUBLICATIONS

Kamel Mamchaoui and Georges Saumon, A method for measuring the oxygen consumption of intact cell monolayers, American Journal of Physiology Lung Cellular and Molecular Physiology (2000) 278: L858-L863.

Derwent Abstract for EP155236, May 25, 2007.

E. Barbera-Guillem, "Overcoming cell culture barriers to meet the demands of cell biology and biotechnology", Reprinted from American Biotechnology Laboratory, May 2001.

"Cell Culture Equipment (Hardware & Devices)", Lab Times, Products, Jan. 2006, pp. 52-58.

* cited by examiner

FLUID FLOW DIVERTER FOR CELL CULTURE VESSEL

FIELD OF THE INVENTION

The present invention relates generally to the cellular biological field and, in particular, to a cell cultivating flask.

BACKGROUND OF THE INVENTION

In vitro culturing of cells provides materials necessary for research in pharmacology, physiology, and toxicology. An exemplary vessel inclusive of a suitable environment for culturing cells is a common laboratory flask. The cells typically attach to and grow on the bottom surface(s) of the flask, immersed in a suitable sustaining media. The flask is then stored in an incubator to maintain the proper temperature and atmosphere for specified growth conditions. Advancements in improving cellular growth conditions, however, have revitalized the standard flask market. With the advent of cell-based high throughput applications, cell culture vessels have been developed to provide an increased surface area for cell growth while also providing necessary gas exchange. These systems employ traditional cell culture vessels including common flasks, roller bottles, cell culture dishes, and multi-layered cell growth devices. In addition, automation permits manipulation of the cell culture vessel or apparatus much like that performed by the manual operator. Current flasks, however, do not allow for complete drainage of fluid from the vessel. Therefore, when removing nutrient media and/or cellular contents from the flask, undesirable fluid (such as cell excretions/waste products, dead-cells contaminants, or other toxins) remains in the vessel. Even if by-products of cellular waste do not pose a significant problem, it is typically necessary to remove and wash all media from the vessel to prevent any inhibitory function of subsequent chemical additives such as trypsin (utilized when harvesting cells from the flask).

Although fluid may be aspirated from the vessel, or the vessel constructed with a sloping feature along the opposite end wall to enable easier removal of media with a canula or pipette tip when-the flask is arranged in position with the neck facing upward, any remaining fluid may still pool at the bottom-most portion of the sloped end wall. This assumes that a canula or tip is capable of extending vertically down from the neck and engaging the opposing end wall. On the other hand, it may be even more so desirable to pour fluid out of the vessel. When pouring liquid contents from a vessel, however, capillary action can cause some of the fluid to be retained in corners or where vessel walls meet perpendicular to each other, including near the drain port where the fluid becomes trapped in the corners of a manifold below the pouring outlet. This can lead to greater fluid retention in the vessel when the fluid clings in these locations rather than moving toward the port. In particular, when pouring liquid volumes from a port, the adherent and coherent properties of the liquid cause different volumes of fluid to be retained in the vessel. Furthermore, fluid that remains in the vessel, such as dead cells, cellular debris or the by-products thereby produced, may contaminate any other growth surface or the replacement media. One solution is to bang the vessel to try to use the fluids momentum to break the capillary force. This can obviously dent or damage the external structure of the flask, however, and possibly disrupt internal structural components of the flask as well, including destruction of internal growth surface areas, or impairment of individual flaskettes internal to the unitary vessel. A canula or syringe tip to collect the remaining media is also not capable of reaching the corner areas of the vessel, especially not flexible or durable enough to withdraw any fluid retained in the hard to reach front corners and edges of the vessel nearest the port.

There is a need for a cell culture vessel that is designed for reducing problems associated with removing fluid from the vessel. The cell culture vessel will assist in draining fluid from the internal surfaces of the vessel, and do so as thoroughly as possible. In addition, the cell culture vessel will reduce fluid retention in the corners of the vessel or near the drain port, further minimizing any contaminating remnants in the vessel during removal of nutrient media or cellular contents. Thus, the fluid will be directed away from internal growth surfaces and toward an outlet or drain port. The cell culture vessel will permit lower fluid retention in its total internal volume and be capable of conforming to current flask designs. The desired cell culture vessel will also be suitable for use in the performance of high throughput assay applications that commonly employ robotic manipulation. Additional advantages will be apparent in the following illustrations and detailed description.

SUMMARY OF THE INVENTION

According to an illustrative embodiment of the present invention, a flask for the efficient culturing of cells is disclosed. The illustrative flask is a cell growth vessel for redirecting a flow of liquid media outward from an internal volume. The vessel comprises a vessel body having one or more walls defining an internal volume for cellular growth; a port in a wall of the vessel body, wherein the port defines an opening or fluid outlet that has a flow of liquid media directed from the internal volume to the port, such as when pouring a liquid medium from the internal volume; and at least one flange positioned in the flow of liquid media, wherein the flange is a construct comprising one or more planar surfaces engaging at least one wall of the vessel body. The improvement of the vessel having a flange or flow diverter in a path of liquid flow outward from the inner surfaces or edges of the internal volume toward the port facilitates removal of substantially all liquid media from the inner surfaces of the vessel body.

Advantageously, the flange engages a wall of the vessel body and extends to a port. In one aspect, the flange engages a bottom wall of the vessel body. The bottom wall may be a surface of the vessel body beneath the port, or a wall underneath the circumferential edge of the port. In another aspect, the flange includes a top surface and 2 planar surfaces that come together at a leading edge. An angle formed between the leading edge of the flange and the wall of the vessel is arranged at an angle less than 180° to facilitate complete drainage of the vessel. An angle of 90°, or less, however, is preferential for directing the flow of fluid outward from the innermost edges and fluid retaining surfaces of the internal vessel. A flange positioned in an inner circumferential portion of the circular opening or pouring outlet may be located anywhere thereabouts; the pouring of the fluid from the outlet determines the wall or portion of the opening for where the flow diverter is created.

In one aspect, a flow diverter is positioned in communication with a manifold. One embodiment includes the flow diverter included in the construction of a manifold that interconnects the individual layers or cell growth chambers in a multi-layered flask. In another aspect, the flow diverter may be symmetrical or unsymmetrical in shape such as when the flange is created to be wider at its base and narrower at a top portion nearest the port (or vice versa).

A method of using the cell growth vessel of the present invention is also disclosed in the application. The method comprises the steps of providing a vessel body having a port that includes at least one flow diverter at a base of the port, filling the vessel with fluid comprising a liquid medium for cellular growth, and removing the liquid medium from the vessel, wherein-the flow diverter redirects the fluid through the port. Tipping or pouring the liquid media across the flow diverter directs the liquid media away from fluid retention areas within the flask. Thus, substantially all of the liquid media is capable of being exhausted from the internal volume of the vessel body. Further benefits and advantages of the disclosed device will apparent in the following descriptions and drawings.

BRIEF DESCRIPTION OF THE DRAWINGS

The invention is best understood from the following detailed description when read with the accompanying drawing figures. It is emphasized that the various features are not necessarily drawn to scale. In fact, the dimensions may be arbitrarily increased or decreased for clarity of discussion.

DETAILED DESCRIPTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known devices and methods may be omitted so as not to obscure the description of the present invention.

Figure 1:
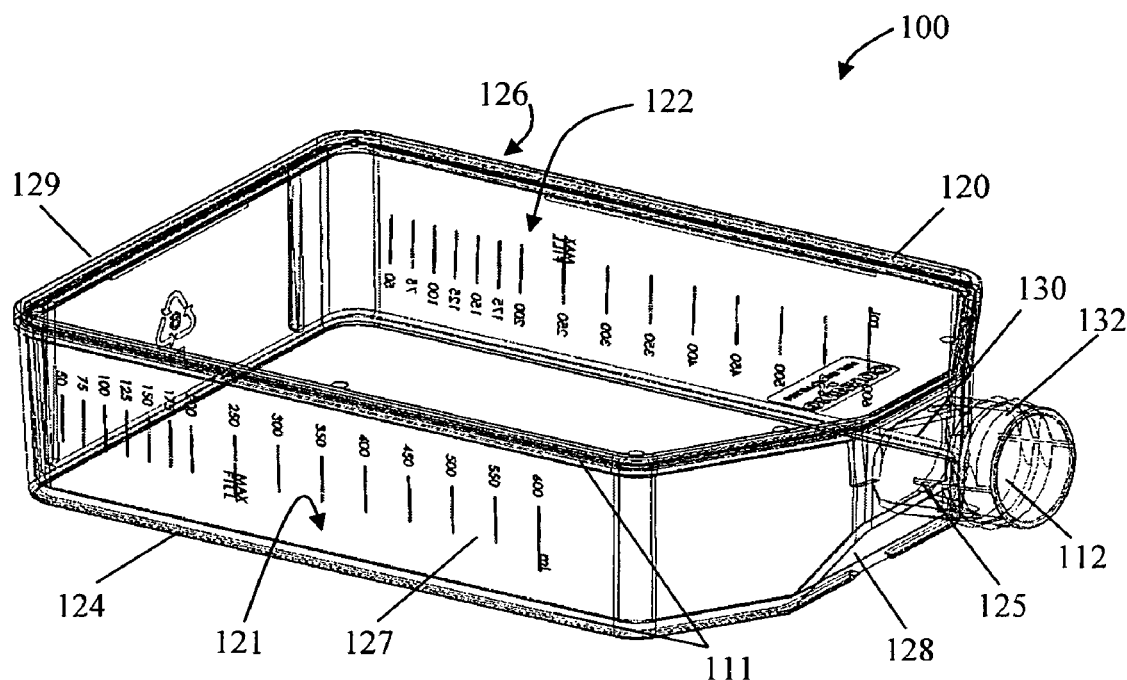
FIG. 1 is a perspective view of an illustrative embodiment of the vessel of the present invention.

Turning to FIG. 1, a vessel 100 of the present invention takes the form of a flask 100. The vessel body 120 comprises a transparent top plate/cover 122 and a bottom tray 124 defining an inner surface or cell growth surface 121 connected at the peripheral edges 111 by sidewalls 126/127, and two end walls 128/129. A port 130 in a first end wall 128 is an opening for filling and draining the vessel 100. In one embodiment of the present invention, the port 130 is included in a neck area 132 of the vessel which is capable of being covered by a-cap. The necked opening 132 in one aspect has an inner neck surface 112 that is elevated from the bottom tray 124. The neck 132 is cylindrical but may be of any size or shape, preferably capable of blocking the entrance or exit of undesired fluid between the interior of the flask and the external environment. The neck may be a straight assembly or canted at an angle and raised from the bottom surface to prevent external contamination. A flow diverter or flange 125 is disposed within an inner circumferential portion 139 of the circular port 130 such that fluid poured from the vessel is directed by the flange base 113 into the outlet/port 130 and out through the neck 132.

Figure 2:
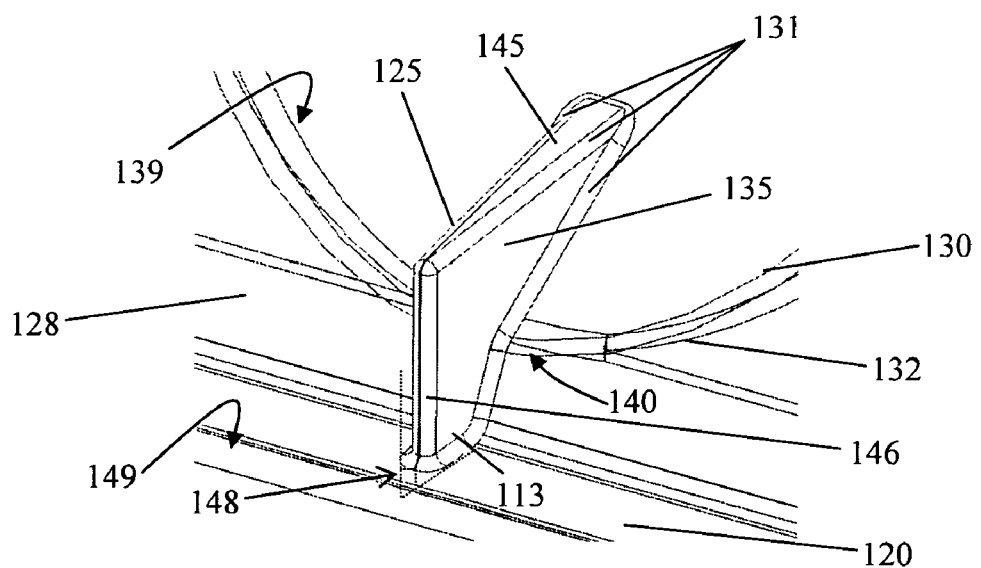
FIG. 2 is a magnified view of an illustrative embodiment of the present invention.

An enlarged perspective view of the flange 125 in FIG. 2 illustrates one aspect of the flow diverter 125 as a construct positioned in the port 130 which is included in the neck 132 of the vessel body 120. The flow diverter construct 125, as illustrated, is a partial wall 125 perpendicular to the inner circumferential portion 139 of the circular port/outlet 130 such that the wall 125 has a top surface 145, a base 113, opposing planar surfaces 135 and gradual contours or transitional surfaces 131 that comply with the structure of the internal vessel body to direct a flow of fluid outward through the drain port 130. In one aspect, the flange is positioned at an angle less than 180° to provide a gradual inclined surface into said port. The gradual incline is defined by gradual sloping of the top surface 145 into the curvature of the neck's inner surface 112. A leading edge 146 where the two planar surfaces 135, the top surface 145, and the base 113 come together is perpendicular to both an end wall 128 and a bottom wall 124/149. The leading edge directs liquid media from the internal vessel outward through the port when the vessel is tipped toward the pouring outlet 130. The angle formed between a bottom wall 149 of the vessel body 120 and the leading edge 146 of the flange 125 therefore should be less than 180°, and even more preferably less than 90° so that the leading edge 146 draws the adhesive properties of the liquid toward the angled junction 148 and the surfaces 135 to direct the liquid out through the port 130 via capillary action. The surface area of the planes 135 may be varied to accommodate surface tensions of various fluids. Any angled niche or curvature 148 may also be created that leads a liquid volume across the planar surfaces 135 to the outlet port. The niche 148 may encompass a wider zone or flange base 113 beneath the port in combination with a bottom wall 149 or may have a broadened top surface 145. It is noted, however, that manufacturing capabilities may prefer production of wider and/or larger moldable parts, particularly for effortless ejection of the parts from the mold. Consequently, a flange 125 may be incorporated with any size and shape of vessel. Transitional surfaces 131 further allow for additional modifications of the flange 125 and enlarge the scope of vessel configurations that can utilize a flange to completely drain a vessel of its liquid contents.

In another embodiment (See FIG. 3), the vessel 300 contains multiple cellular growth surfaces 310 in chambers 311. The plurality of cell growth chambers 311, as illustrated, can be multiple flaskettes 311 integral with a unitary vessel body 320. The vessel of this embodiment comprises an outer unitary vessel body 320 defined by a top plate 322, a bottom tray 324, sidewalls 312, and end walls 314. Tracheal spaces 318 are created between each cell growth chamber 311 and are separated from each chamber 311 by gas permeable, liquid impermeable surfaces. As illustrated, each cell growth chamber 311 alternates with a tracheal chamber 318 in vertical successive orientation. Accessibility to the cellular growth chambers 311 is achieved via an aperture/opening 330 within the flask body 320. The aperture 330 creating a necked opening 332 is connected to the cell growth chambers 311 via a manifold 304. The manifold 304 is a portal for manipulation of flask contents. Flow diverters 325 are positioned with the manifold 304 so that draining of fluid from the flaskettes 311 through the necked opening 332 is efficiently directed across the transitional surfaces 331/334 of each corresponding flow diverter 325 (as dependent on the directionality of pouring from the neck). The transitional surfaces are defined by curved 331 or flat 334 planar edges of the flow diverter wall 325 or gradual contours 331/334 that allow for the flow diverter 325 to be incorporated as a partial wall 325 with the exit opening 330. Multiple flow diverters 325 may permit fluid in the vessel to be poured out through the opening in any direction. In this embodiment, it would be preferable for the fluid to be poured from a top or bottom side of the necked opening since (as relative to the illustrative perspective as shown). In one aspect, the transitional surface 331/334 of the planar construct 325 extends in at least two dimensions to accommodate adhesive and cohesive properties or the fluid. However, the transitional surfaces 331/334 may be defined by any flat or curved surface that is in an area continuous with a base surface of the flask. The base surface of the flask may be defined as the area which permits fluid flow across a lower surface of the flask, assuming gravity keeps fluid flow in a base area of the flask no matter which angle or side the flask is directed. In addition, the necked opening 332 in this embodiment is also capable of being covered by a cap, thus allowing the flask to be completely filled with media without leakage. Any cap or septa may be compliant with flasks of the present invention.

The vessels 100, 300 of the present invention may be made by any number of acceptable manufacturing methods well known to those of skill in the art. In a preferred method, the vessel 100/300 is assembled from a collection-of separately injection molded parts. Though any polymer suitable for molding and commonly utilized in the manufacture of laboratory ware may be used, polystyrene is preferred. As in FIG. 3, the bottom tray 324 and top plate 322 are preferably injection molded. Various sizes and shapes of supports 340 may be incorporated to facilitate positioning of the membranous layers 310 for cell culture within the internal flask body 320. The supports 340 are generally rigid structures to support a sheet of gas permeable membrane 310 adhered to the frame body 320, as well as provide a structural framework to allow multiple layers (rigid or membranous 310) to be formed within the flask 300. The flow diverter 325 is preferably molded with a portion of the vessel body such as with the bottom tray. However, the flow diverter 325 can be properly affixed to an internal surface of the vessel by any number of methods including but not limited to adhesive or solvent bonding, heat sealing or welding, compression, ultrasonic welding, laser welding and/or any other method commonly used for generating seals between parts. Laser welding preferentially ensures a continuous transitional surface 331/334 having contours flush with and fused to the vessel 300 to ensure that the flow diverter 325 becomes an integral portion of the interior surface of the apparatus/vessel. Advantageously and in order to enhance cell attachment and growth, the surfaces internal to the vessel are treated to enable cell growth. Treatment may be accomplished by any number of methods known in the art which include plasma discharge, corona discharge, gas plasma discharge, ion bombardment, ionizing radiation, and high intensity UV light.

Finally, the vessel may be sealed from direct external access by way of a cap, including any screw cap, snap-fit cap, cap with septum, cap with air holes, or any cap known in the art. The cap does not interfere with the flow diverter 125/325. In fact, any closure for the vessel port or openings 130/330 will be compliant with the structural modifications of the transitional surfaces and contours of the flow diverter 325. Preferably, a cap is utilized in which a septum is integral with the cap. This will allow a canula, tip or needle to access the contents of the apparatus 100/300 without the need for unscrewing the cap. Partial septa, however, would allocate where a tip would unobtrusively enter the opening of the high density growth vessel 300 without interfering with any constructs that create the flow diverter. The septum is leak proof, puncturable and capable of resealing once the needle, tip or canula is removed from the apparatus, even after multiple punctures. In one embodiment, the cap is positioned to access the contents of the apparatus 100 via an end wall 128/129. In addition, the cap may be positioned on a top surface 122. Further, the cap arrangement can also be located such that the cap-does not protrude from the rectangular footprint as determined by the periphery of the vessel 100. Other accessibility options may include a neck and cap arrangement within a corner region of the apparatus 100, such that the cap would not protrude from the periphery of the vessel body 120.

In use, vessels 100/300 of the current invention are employed according to accepted cell growth methods. Cells are introduced to the vessels 100/300 though the aperture 130/330, respectively, via the neck (or through a septum in the aperture). Along with the cells, media is introduced such that the cells are immersed in the media. During periods of cellular growth, the vessel may be incubated at specified environmental growth conditions and removed in a continuous cycling timeframe so that media and/or cells can be replenished. Therefore, during the cell growth process, it may become necessary to extract the exhausted media and insert fresh media. As previously described, media replacement may be partially achieved through insertion of a canula, for example, through the septum. Thorough removal of media, however, may be accomplished by removing the cap, in embodiments that offer this option, and pouring the internal fluids of the vessel out through the drain port across the flow diverter. The flow diverter assists in draining the fluid away from all internal surfaces of the vessel by utilizing the capillary attraction along the wall of the flow diverter and leading the fluid flow out of the vessel. Since all corners of the vessel do not feed directly into the drain port, the partial wall of the flow diverter addresses this problem. Thus, substantially all fluid is drained away from retaining corners or restricting surfaces within the vessel, allowing fresh media to be replenished without worry of contamination from the left-behind cellular remnants. The pouring step quickly and easily drains the fluid from the vessel, improving the efficiency of the flask. Media can then be thoroughly drained and repeatedly filled and drained again until the cells are ready for harvesting. Completely removing all media (and/or any wash material that may ensue in a following step) from the internal surfaces of the vessel further eliminates any inhibitory effect that the undesirable fluid may have on subsequently added chemical substances. Thus, it is advantageous for the vessel to be capable exhausting substantially all liquid volumes from the internal volume. A chemical additive such as trypsin can then be injected through a septum or through an open port which causes the attachment dependent cell to release from the growth surfaces of the vessel. The cells can then be harvested from the flask in the same manner as the media is drained or by scraping the internal cell growth surfaces.

Figure 3:
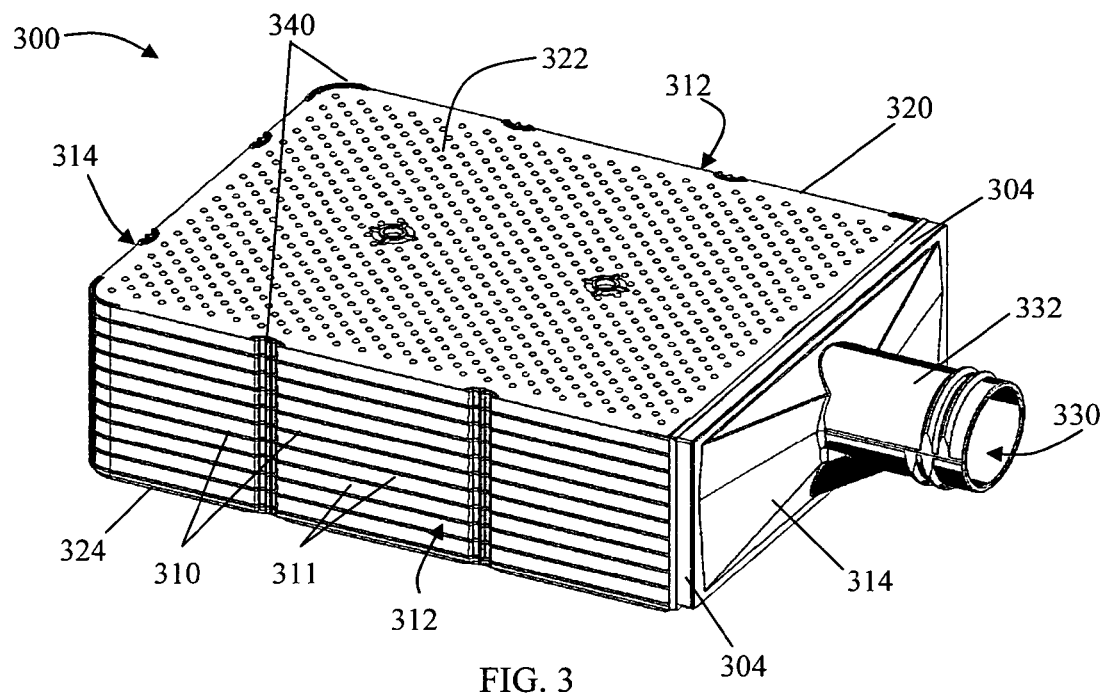
FIG. 3 is a perspective view of an embodiment of the present invention.
Figure 4:
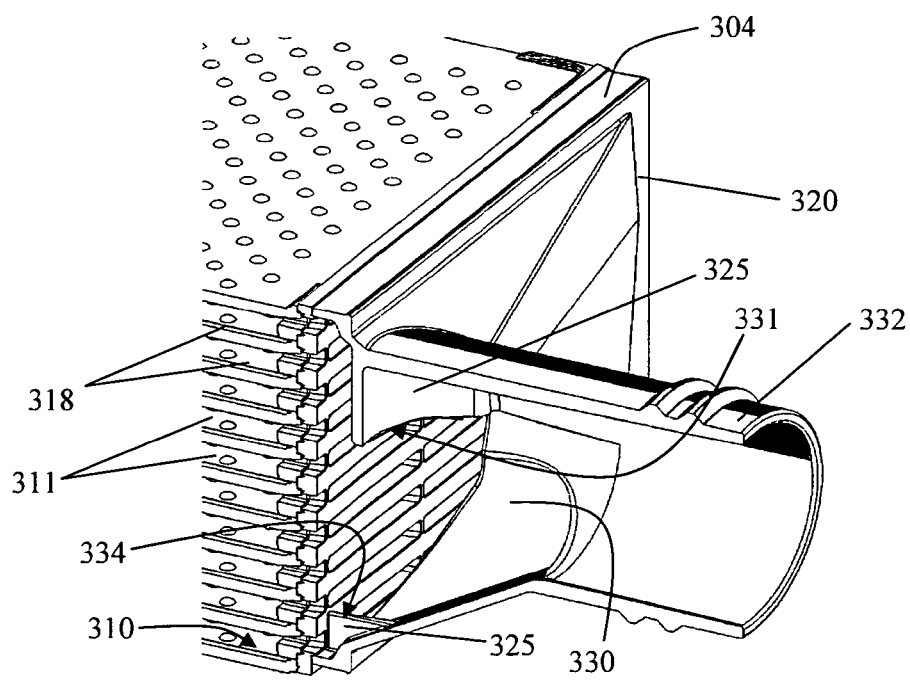
FIG. 4 is a magnified cross-sectional view of an embodiment of the present invention.

As illustrated in FIG. 3, an embodiment of the present invention utilizes a manifold 304 that permits access to the internal cell culture layers. The manifold in one aspect is a separate compartment that integrally connects the multiple cell culture chambers 311 and tracheal chambers 318 with a necked opening 332. A flow diverter 325 positioned in the neck opening therefore offers further advantages of draining the manifold area when media is poured from the neck. Utilization of the vessel 300 may also be employed in accordance with accepted cell growth culturing. As discussed in a previous embodiment, cells are introduced to the flask through the neck or through the septum. Along with the cells, media is introduced such that the cells are immersed in the media. The vessel is arranged such that the cell-containing media covers the cell growth surfaces. Advantageously, the vessel is capable of being completely filled with media since the gas permeable membranes are capable of providing uniform gas distribution to the cell growth surfaces. The apparatus is then placed within an incubator and may be stacked with similar flasks. As it becomes necessary to extract the exhausted media and insert fresh media, the media can be directly poured across the flow diverter and toward the draining outlet.

As presented, embodiments of the present invention offer several improvements over standard vessels currently used in industry. The improved cell culture vessel is designed to reduce problems associated with removing fluid from the vessel by exhausting substantially all fluid from the vessel during and after cell cultivation. The cell culture vessel assists in draining fluid from the internal surfaces of cellular growth, including areas difficult to reach by a pipette tip as well as corner areas restricted by capillary forces of the liquid volume. In addition, fluid retention is reduced in the corners of the vessel and near the drain port by drawing adhesive and cohesive forces of the liquid contents nearer the drain port, in a direction toward an outlet or drain port, by way of the flow diverter. Furthermore, any undesirable/contaminant liquid material that remains in adherence with an internal surface of the vessel is minimized by the thorough exhaustion/removal of the liquid volume between media replacement steps. The cell culture vessel lowers the amount of fluid retained in its overall internal volume and is capable of conforming to current and modified flask designs. The desired cell culture vessel is also suitable for use in the performance of high throughput assay applications that commonly employ robotic manipulation since the external structural surfaces of the vessel are not presumably affected.

Supplementary, constructs or flanges 125 may be formed above and/or below the cell growth surfaces or below the circumferential rim 140 of the port opening 130 and internal to the vessel body 120 or manifold. In view of that, it may be beneficial to leave the port open (without any walls or surfaces created therein which could alternatively obstruct the opening) by constructing a flow diverter or flange that is engaged with a wall of the vessel body and contacting an outer rim 140 of the port, such that modified planar surfaces 135, contours or transitional surfaces 131 of the of the flange are continuous with the conformations of a bottom wall 149 of the vessel body and the outlet port. In turn, any wall or surface which is in contact with the fluid flow (when fluid is being exhausted from the vessel) is accommodated by the transitional surfaces or contours of the flange that direct fluid away from internal cellular growth areas.

The flow diverter wall may also be constructed to partially fill any gap at the base of a port (the base defined by gravity as the lower portion or bottom wall that contacts the liquid being poured from a vessel port); or fully lengthen at any diameter of an aperture. A diversified network of supports, intersecting or alternating gas permeable membrane arrangements with supports and air/tracheal spaces in the multi-layered vessel may also be adapted to include any number of flow diverter constructs, in any size, shape, or dimension. Thus, embodiments of the present invention as described may be modified to take the shape of any device, container, apparatus, vessel, or flask currently used in industry. Specifically, cylindrical or alternative vessels may utilize flow diverters in combination with tracheal chambers or spaces to provide an improved culturing environment for the growth of cells. Further, the flow diverters may be incorporated into the passageway-like chambers of a cell growth vessel. Since tracheal spaces or air chambers in combination with the chamber passages may be utilized for perfusion, alternative approaches may possibly include passageways directed toward the flow diverter, or the flow diverter itself constructed integrally with the passageways.

Hence, embodiments of the present invention are for exemplary purposes only and not further limitation. As discussed, the vessel may include any unitary structure, apparatus, device or flask with the capacity to integrally incorporate a flow diverter or construct in an opening used for fluid removal. The invention being thus described, it would be obvious that the same may be varied in many ways by one of ordinary skill in the art having had the benefit of the present disclosure. Such variations are not regarded as a departure from the spirit and scope of the invention, and such modifications as would be obvious to one skilled in the art are intended to be included within the scope of the following claims and their legal equivalents.

The invention claimed is:

1. A cell growth vessel comprising:
a vessel body having one or more walls defining an internal volume for cell growth;
a port in at least one said wall of said vessel body, wherein said port defines a fluid outlet; and
at least one flange,
wherein said flange extends from an internal surface of said port to an internal surface of one or more walls; and,
wherein said flange comprises a top surface, two opposing surfaces and one or more transitional surfaces defining a three dimensional structure interconnecting said internal surface of said port with said internal surface of said one or more walls of said vessel body.

2. The cell growth vessel of claim 1, wherein said flange engages said vessel body on a bottom wall.

3. The cell growth vessel of claim 1, wherein said flange further comprises a leading edge.

4. The cell growth vessel of claim 3, wherein said leading edge is arranged at an angle less than 180° with said bottom wall of said vessel.

5. The cell growth vessel of claim 3, wherein said leading edge is arranged at an angle of 90° or less with said bottom wall of said vessel body.

6. The cell growth vessel of claim 3, wherein said flange is broader where it attaches to said internal surfaces than at the leading edge or the top surface.

7. The cell growth vessel of claim 1, wherein said flange comprises transitional surfaces continuous with an inner surface of a bottom wall of said vessel body.

8. The cell growth vessel of claim 1, wherein said top surface of said flange provides a gradual incline into said port.

9. The cell growth vessel of claim 1, wherein said port comprises a circular port.

10. The cell growth vessel of claim 9, wherein said port comprises a cylindrical neck portion extending from said vessel body and wherein said flange extends from said bottom wall of said vessel body into an inner circumferential portion of the circular port.

11. The cell growth vessel of claim 1, wherein said flange is a partial wall at a base of said port.

12. The cell growth vessel of claim 1, wherein said internal volume includes one or more cell growth surfaces.

13. The cell growth vessel according to claim 1, wherein vessel body further comprises a manifold structured and arranged to provide fluid communication between the port and one or more cell growth surfaces.

14. A cell growth vessel according to claim 13 wherein the manifold comprises an end wall.

15. A cell growth vessel according to claim 1, wherein said transitional surfaces comprises flat or curved surfaces connecting said flange to said internal surface of said port or said internal surface of said one or mor walls or a combination.

* * * * *